United States Patent [19]

Teske

[11] Patent Number: 5,503,720

[45] Date of Patent: Apr. 2, 1996

[54] PROCESS FOR THE QUANTITATIVE DETERMINATION OF ELECTROCHEMICALLY REDUCIBLE OR OXIDIZABLE SUBSTANCES, PARTICULARLY PERACETIC ACID MIXED WITH OTHER OXIDIZING SUBSTANCES

[75] Inventor: Gunter Teske, Berlin, Germany

[73] Assignee: Dr. Thiedig & Co., Berline, Germany

[21] Appl. No.: 355,059

[22] Filed: Dec. 13, 1994

[30]     Foreign Application Priority Data

Dec. 15, 1993 [DE] Germany ............................ 43 42 787.1

[51] Int. Cl.⁶ ..................................................... G01N 27/26
[52] U.S. Cl. .......................... 205/787; 204/412; 204/403; 204/415; 204/406; 204/409; 436/52; 436/124; 436/149; 436/150
[58] Field of Search ............................ 204/153.2, 153.12, 204/153.1, 412, 403, 415, 406, 409; 436/52, 124, 149, 150

[56]                References Cited

U.S. PATENT DOCUMENTS 5,395,493   3/1995   Pinkowski ........................... 204/153.2

FOREIGN PATENT DOCUMENTS 4223228   1/1994   European Pat. Off. .

Primary Examiner—Bruce F. Bell
Attorney, Agent, or Firm—Marshall & Melhorn

[57]                  ABSTRACT

A process for the quantitative determination of oxidizing and reducing substances is described, also mixed with chemically similarly reacting substances, particularly peracetic acid mixed with further substances such as hydrogen peroxide ($H_2O_2$) and/or acetic acid by means of per se known potentiostatic amperometry, in which the determination takes place with a test electrode voltage, which, independently of the prevailing reaction mechanism, is below the diffusion limiting current range between the no-load voltage and the flex point of the current density-voltage curve. The peracetic acid determination takes place at a current density of <5%, preferably <1% of the limiting current density.

20 Claims, 3 Drawing Sheets 5,503,720

PROCESS FOR THE QUANTITATIVE DETERMINATION OF ELECTROCHEMICALLY REDUCIBLE OR OXIDIZABLE SUBSTANCES, PARTICULARLY PERACETIC ACID MIXED WITH OTHER OXIDIZING SUBSTANCES

BACKGROUND OF THE INVENTION

1. Field of Invention

The invention relates to an electrochemical process performed with a constant, regulated voltage of the test electrode for the selective determination of in particular peracetic acid mixed with other oxidants, such as e.g. $H_2O_2$, as well as other substances, a corresponding potentiostatic apparatus for performing the process and the use of the process for the continuous measurement of process flows containing peracetic acid.

2. Description of the Prior Art

The strict requirements made regarding the quality control of foods and beverages (cf. minimum keeping quality) inter alia make necessary the most careful procedures when cleaning and disinfecting the corresponding production and processing plants, e.g. for milk, beer and soft drinks. In order to ensure the necessary sterility the containers, pipes, pumps, filters and filling devices must be regularly treated with cleaning agents (e.g. acids and lyes) and disinfecting solutions. The said plants must then be rinsed free with clean water in order to avoid inadmissible actions on the products by harmful impurities. For this purpose use is frequently made of CIP processes in various technical forms. The cleaning and disinfecting solutions can be discarded after passing through the plants (usually in the case of smaller systems) or can be returned to holding tanks for rational reuse. At this point there is a supplementing of the spent active substances.

Prior to entering the plants the disinfectants must have the concentrations necessary for an adequate activity. It can also be useful to know the active substance losses in the individual plant parts and/or in the drains. For rational water consumption purposes it is useful to determine the time of adequate free rinsing of the plant. It is necessary to prove that the actual products are not contaminated. It is important for the corresponding analysis which disinfectants are used for solving the complex measurement problem.

Peracetic acid ($CH_3COOOH$), mixed with hydrogen peroxide ($H_2O_2$) and acetic acid ($CH_3COOH$), is being increasingly used as a strong, oxidatively acting disinfectant. It therefore replaces chlorine-containing substances, quaternary ammonium compounds and expensive ozone. The broad action spectrum against microorganisms (bacteria, fungi, viruses), even at low temperatures, the usually problem-free reduction product acetic acid ($CH_3COOOH \rightarrow CH_3COOH + \frac{1}{2} O_2$), as well as the complete degradability thereof in biological sewage treatment plants are excellent and convincing advantageous characteristics, in addition to the relatively easy production process.

Concentrates with different active substance concentrations are marketed on the basis of peracetic acids. Correspondingly to the production from high percentage hydrogen peroxide and concentrated acetic acid, equilibrium concentrations are obtained with a peracetic percentage between 3 and 40%. The addition of stabilizers (often phosphonic acids) slows down the self-decomposition of these substances.

To part of said commercial products are also added mineral acids (sulphuric/nitric acid). The disinfecting solutions used are prepared from these concentrates by diluting in a ratio of 1:100 to 1:1000, giving peracetic acid concentrations between 100 and 2000 ppm (mg/l).

For the analytical determination of peracetic acid concentrations in these ranges, use is almost exclusively made of a titration process. In the latter, firstly by titration with potassium permanganate solution the $H_2O_2$ content is determined and then eliminated. This is followed by peracetic acid titration with sodium thiosulphate solutions against iodine strength as the indicator. Complicated photometric determination methods or the evaluation of luminescence effects are too complicated and costly for operational measuring technology in connection with disinfecting measures.

The use of test strips with colour indicators is simple and fast, but often requires dilution and the results are often not very accurate.

For the continuous measurement of the peracetic acid, which is extremely important for operationally reliable and rational use, no suitable process has been available up to now. Solely for the detection of the risk of the contamination of beverages, use is made operationally of conductivity measuring processes, but these require the aforementioned addition of mineral acids to the disinfectants.

German Patent DE 4,223,228 A1 describes a cyclovoltametrically operating process for the determination of per acids, as well as $H_2O_2$, in which the potential difference of two electrodes in the central third of the double layer range is chosen. Through a voltage-dynamic procedure a cathodic maximum of the current signal which occurs is determined and which is essentially associated with the per acid content of the electrolyte, i.e. the solution. The optimum potential difference must be cyclovoltametrically, iteratively determined.

The current-voltage characteristic of this potentiodynamic procedure performed with high change speeds for the voltage in the double layer range mainly undergo determination by capacitive currents and processes of adsorption and desorption, which are accompanied by charge conversion.

Thus, in summarizing, it can be established that hitherto no suitable measuring process is known, which is able to solve the aforementioned measuring problems, particularly through the indication of a constantly up-dated measured value.

Therefore the problem of the invention is to be able to measure peracetic acid with high excesses (up to 10 times and more) of other oxidants such as $H_2O_2$ in a selective and continuous manner, particularly in a peracetic acid concentration range of 10 to 2000 ppm.

SUMMARY OF THE INVENTION

With respect to the process this problem is solved by the quantitative determination of oxidizing and reducing substances with a test electrode voltage that is independent of the prevailing reaction mechanism. With respect to the apparatus for performing the process the apparatus includes a test cell with a potentiostatically operating three-electrode arrangement with a counterelectrode, a test electrode, and a reference electrode behind a diaphragm. Advantageous further developments are disclosed in the subclaims.

Surprisingly and without respecting the viewpoint prevailing for electrochemical measuring technology, according to which a concentration determination by potentiostatic amperometry must exclusively take place in the diffusion limiting current range, it has been found that also below the limiting current range, particularly in the case of measuring voltages between the off-load voltage R (current density→0) and the flex point $W_k$ of the current density-voltage curve, quantitative determinations, e.g. of peracetic acid, $H_2O_2$ and other substances are possible in reproducible, accurate manner, i.e. in calibratable manner (cf. FIG. 4). The conditions imposed on the continuous measuring process are fulfilled. There is little or no drift from the zero and the measuring sensitivity of the sensor, there is a rapid response to concentration changes, selectivity and decisively the calibratable dependence of the measuring signal on the concentration of the substance to be determined. Independently of the prevailing reaction mechanism (e.g. passage-controlled and/or reaction-controlled), hitherto this voltage range has been unusable for amperometric purposes, because a number of theoretically proved reasons (K. J. Vetter in the journal "Elektrochemische Kinetic", Section 48, p.99 ff) appeared to make impossible a stable measurement of concentrations. Contrary to this established standpoint it has now been found that the determination of peracetic acid, even if further substances are present in excess such as $H_2O_2$ and/or acetic acid, with a current density of <5%, preferably <1% of the peracetic acid diffusion limiting current density of a freshly activated test electrode is in fact possible. It is particularly surprising that if such small current densities are present, a stationary state of the test electrode is reached and over a long period of time, namely several weeks, the dependence of the current density on the peracetic acid concentration is virtually constant and therefore calibratable. Therefore accurate and reproducible measurements can be made in this range. The stationary state, which is potentiostatic, i.e. with a constant voltage of the test electrode, means that only faradic currents linked with the present reducing substance conversions are vital. This surprising, unexpected finding now makes available this range of the stationary current-voltage curve parts between the no-load voltage and the flex point for solving the set and other problems.

This finding is independent of the reaction mechanism prevailing in this range and is inter alia characterized in that the current density is completely or almost completely independent of the movement state of the electrolyte with respect to the electrode system and there is a strong temperature influence on the substance conversion at the test electrode (approximately +15% per 1° C. up to 20° C.).

According to preferred embodiments, it is now proposed that for obtaining such low current densities the determination takes place at measuring voltages higher than 100 mV, preferably at 150 to 350 mV and with particular preference at around 280 mV relative to the Ag/AgCl electrode. Through the application of such a measuring voltage corresponding peracetic acid current densities of <5%, preferably <1% relative to the limiting current density of a freshly activated test electrode are obtained and the further substances present in excess and in particular $H_2O_2$ no longer make any contribution to the current density, so that the peracetic acid measurement can take place selectively.

The measuring process can be performed with per se known, potentiostatically operating and amperomatic devices. It has proved advantageous if the test cell has three electrodes, namely a counterelectrode, a test electrode and a reference electrode.

Due to the fact that reproducible and accurate measured results can be obtained with such low peracetic acid current densities, the proposed process is particularly suitable for continuous, selective concentration measurements of peracetic acid mixed with $H_2O_2$, as well as other substances, also in the presence of chemically similarly reacting substances.

BRIEF DESCRIPTION OF THE DRAWINGS

Further features, details and advantages of the invention can be gathered from the following description of an embodiment of the invention and the attached drawings, wherein show.

DESCRIPTION OF THE PREFERRED EMBODIMENT

For performing the measurements use was made of a modified apparatus of type EC 401S of Dr. Thiedig & Co.

Figure 1:
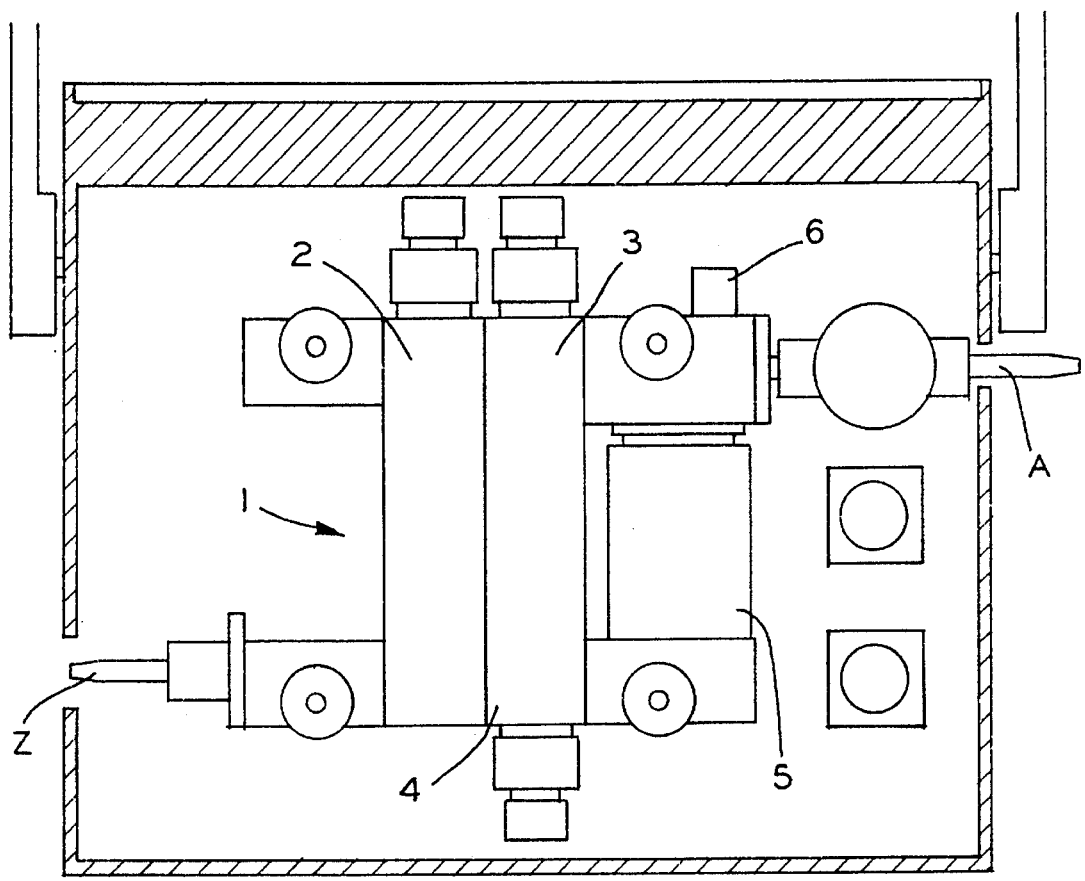
FIG. 1 the basic construction of the Digox measuring apparatus.

FIG. 1 shows its basic construction. The apparatus comprises a test cell 1 with a test electrode 3, a reference electrode 2 and a counterelectrode 4. Further details of the structure can be gathered from FIG. 2. The supply of the process flow takes place with the supply line Z. The liquid flow is passed through the test cell 1 and via the outlet A. The apparatus also has a temperature sensor 6 and a flowmeter 5.

Figure 2:
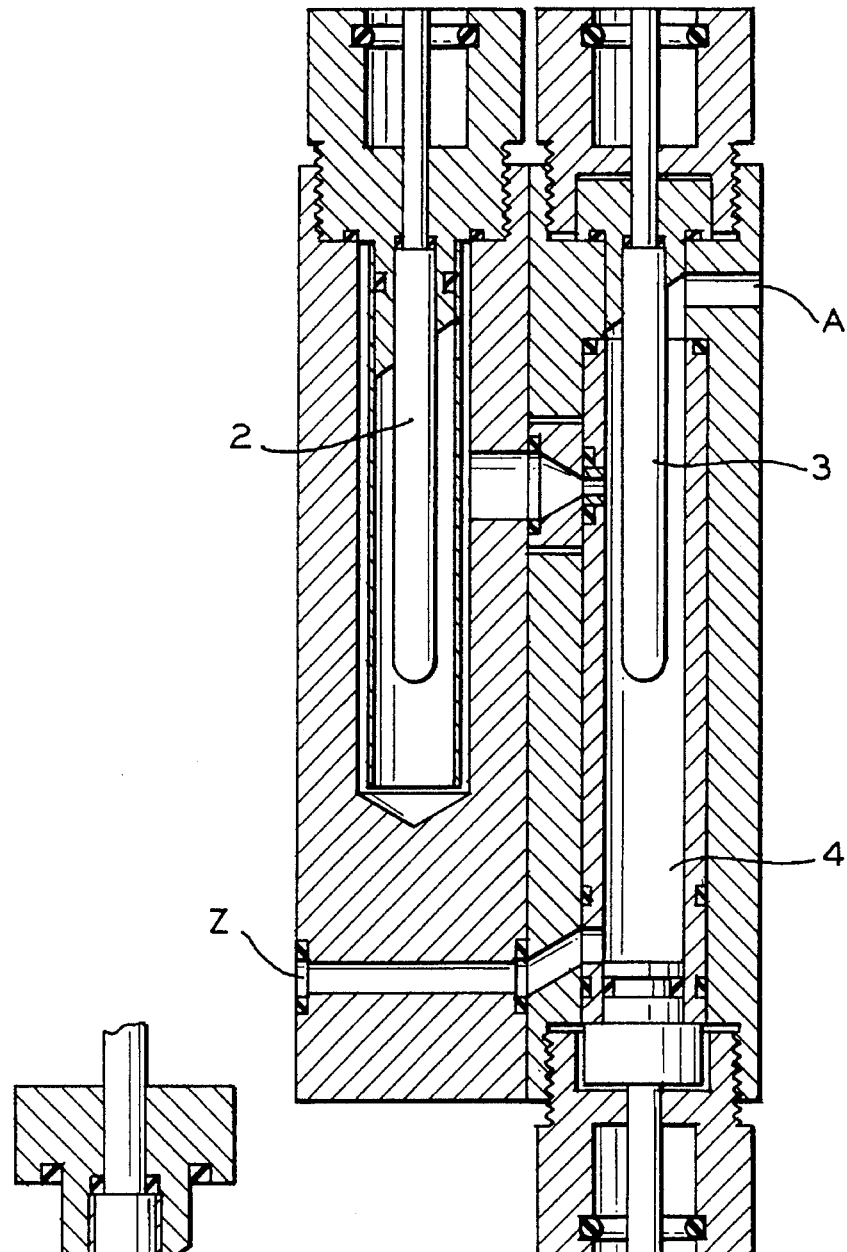
FIG. 2 the structure of the test cell.

FIG. 2 shows the precise construction of the test cell with the test electrode 3, the reference electrode 2 and the counterelectrode 4. The reference electrode 2 is positioned behind a membrane formed by a clay diaphragm 7 in test cell 1.

Figure 3:
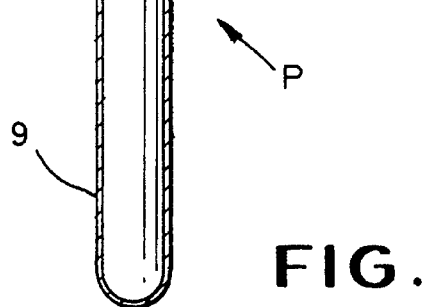
FIG. 3 the P test electrode.
Figure 4:
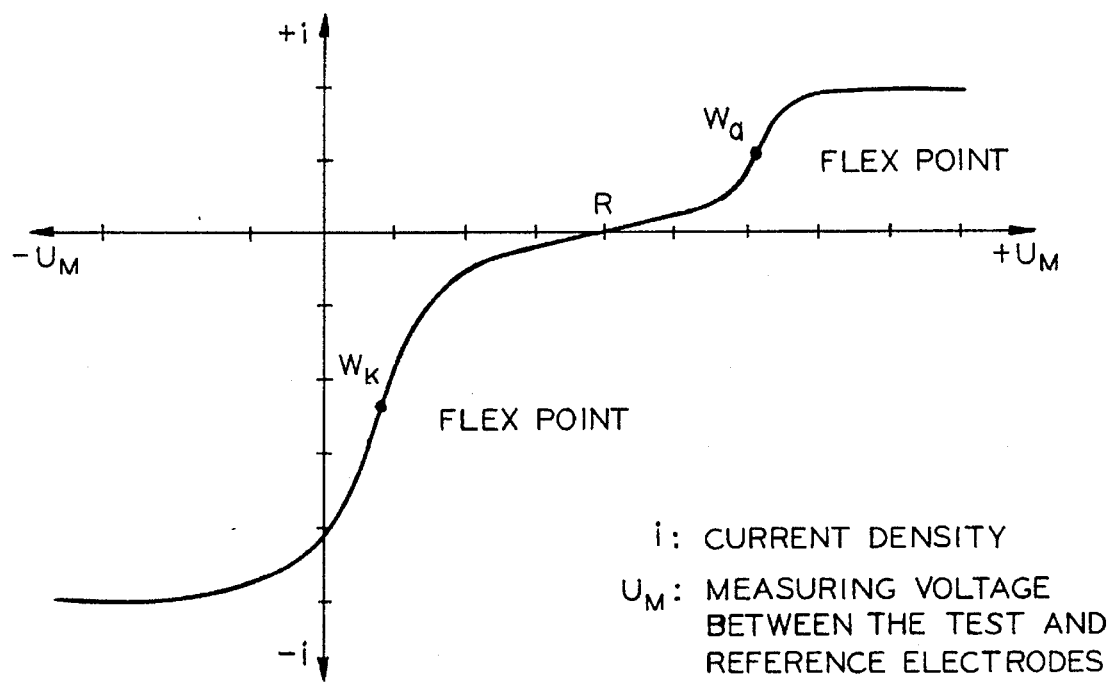
FIG. 4 the current density/voltage curve.

As the preferred test electrode use is made of the test electrode P (FIG. 3) having a surface area of 8.35 cm². The test electrode P has a solid gold jacket 9 and is engaged over a high-grade steel core. The two materials are connected and bonded together in the vicinity of the short tube.

For the use of the test electrode P it would also be possible to use the mass-produced counterelectrode from the Digox EC 401S apparatus having an internal diameter of 10 mm, together with the associated diaphragm.

The reference electrode used was a silver/silver chloride electrode.

With the above-described apparatus continuous peracetic acid measurements were performed with the concentration of the hydrogen peroxide and other substances in solution being ten times that of the peracetic acid. For the better understanding of the measurement results hereinafter details are given of certain voltametric and amperometric concentration measuring processes.

As stated hereinbefore it was hitherto only possible to measure within the diffusion limiting current range. According to the standpoints held up to now the linear proportionality between the measuring current and the concentration of the test component, as well as the long-term stability of the measuring signal are only ensured in said range. This is based on the principles of polarography on which all such processes are based. These measurement conditions are characterized by a strong dependence of the measuring current on the relative movement of the electrolyte with respect to the test electrode. To obtain reproducible and accurate measured results it is vital to keep the current conditions at the electrode constant. It has been revealed that when comparing the diffusion limiting current ranges of peracetic acid and hydrogen peroxide after recording their current-voltage curves, there was a complete superimposing in all the pH-ranges. It is therefore understandable that no selective measurement can take place in the peracetic acid diffusion limiting current range. Admittedly in certain ranges the current densities for peracetic acid, based on the concentration in mg/l, are much higher than for the same concentrations of $H_2O_2$, but the present problem case is characterized in that the $H_2O_2$ is present in much higher concentrations (up to 10 times and more) than the peracetic acid. With concentration conditions close to those in practice the current proportions of peracetic acid to $H_2O_2$ were 3:1 in the most favourable case. Thus, under these conditions the necessary selectivity for determining peracetic acid concentrations does not exist.

Fundamentally there are various possibilities for getting a round this dilemma, namely by removing the $H_2O_2$ either chemically or by other processes, so as to permit a selective measurement of peracetic acid in the limiting current range.

The applicant has been able to prove that voltage ranges exist, in which the current densities for hydrogen peroxide reduction drop to such an extent that they can be ignored compared with the current densities for peracetic acid. It has been found that with peracetic acid current densities of below 1% of the limiting current density the corresponding hydrogen peroxide current density was more than two powers of 10 lower, i.e. it was close to the exchange current density.

Table 1 provides a survey of the tests performed at different measuring voltages and makes it clear that when performing the measurement with voltages of >130 mV preferably in the range 280 mV, the measuring current density of $H_2O_2$ is negligible. Thus, in the case of measuring voltages of at least >100 mV a reliable, reproducible and accurate measurement of peracetic acid is possible, even when the concentration of the hydrogen peroxide in solution is ten times that of the peracetic acid.

is possible to show that by appropriate pretreatment measures this long decay phase can be shortened. It has proved advantageous to carry out a prepolarization of the test electrode in solutions, containing on a maximum 10 to 30 times more peracetic acid than the test solutions. This electrochemical pretreatment is maintained for approximately 0.5 to 3 h. The test electrode is then polished dry with filter paper and can then again be used in the measuring system. The stationary state is then reached after 2 to 10 h. Therefore the freshly activated test electrode is available as a calibratable sensor in a much shorter time than was initially expected.

Figure 5:
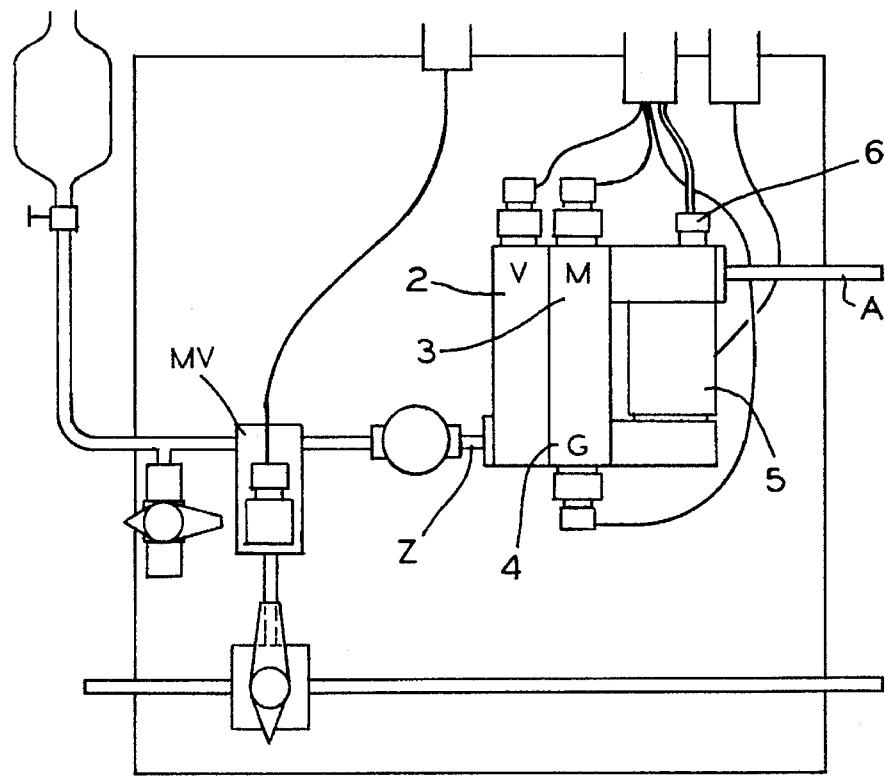
FIG. 5 a diagrammatic representation of the test arrangement.

The calibration check is carried out every so often, in that (cf. FIG. 5) the test cell MG is automatically provided via a solenoid valve MV with a calibration with known peracetic acid concentration (desired value). The reading on the not shown display is matched by means of a microprocessor to the previously inputted desired value and consequently any measuring sensitivity changes are corrected.

A particular characteristic of the process is that it can be used continuously. Particular preference is given to the use of this process for determining peracetic acid in disinfectants in the previously described mixtures, particularly with $H_2O_2$ and acetic acid.

I claim:

1. A process for the quantitative determination of peracetic acid in a solution by potentiostatic amperometry, characterized by delivering a peracetic acid mixed with hydrogen peroxide or acetic acid, or both, to a potentiostatically operating three-electrode test cell arrangement with a counterelectrode, a test electrode, and a reference electrode; and conducting a potentiostatic amperometry determination at a test electrode voltage, which, independently of a prevailing reaction mechanism, is below a diffusion limiting current range between a no-load voltage and flex points of a current density-voltage curve.

2. The process according to claim 1, wherein the determination of the peracetic acid takes place at a current density of less than 5% of the diffusion limiting current range.

3. The process according to claim 1, wherein the deter-

TABLE 1

| Measuring Voltage | Measuring current density peracetic acid μA/cm² per 100 ppm | Measuring current density $H_2O_2$ μA/cm² per 100 ppm | Measuring current proportion in a PES:$H_2O_2$ ratio 1:1 | Measuring current proportion in a PES:$H_2O_2$ ratio 1:10 | Measuring current proportion in a PES:$H_2O_2$ ratio 1:100 |
|---|---|---|---|---|---|
| +70 | 440 | 140 | 75:25 | 24:76 | 3:97 |
| +130 | 1.51 | 0.024 | 98:2 | 86:14 | 39:61 |
| +280 | 0.08 = 0.01 | 0.0008 = 0.0001 | 99:1 | 92:8 | 54:46 |

If in the case of permanent use as a result of mechanical impurities or other activity influences of the measuring or test electrode the current density has dropped to such an extent that e.g. in a calibration check the modulation of the reading to the desired value is no longer possible, an activation of the test electrode is necessary. This can take place by polishing with abrasive cloths, which are preferably coated with an iron oxide powder. Practical tests have revealed that the current density of a freshly activated test electrode was relatively high and in the case of a constant peracetic acid concentration and constant temperature, it dropped to a value below 5% of this initial current over 60 to 120 h.

Any further changes were then only very small and it was possible to assume over several weeks an almost constant current density, i.e. a stationary electrode state. However, it mination of the peracetic acid takes place at a measuring voltage of greater than 100 millivolts, measured relative to the reference electrode.

4. The process according to claim 1, wherein the determination of the peracetic acid takes place at a measuring voltage in the range of 150 to 350 millivolts, measured relative to the reference voltage.

5. The process according to claim 1, wherein the determination of the peracetic acid takes place at a current density of less than 5% of the diffusion limiting current range and at a measuring voltage in the range of 150 to 350 millivolts, measured relative to the reference voltage.

6. The process according to claim 1, wherein the determination of the peracetic acid takes place at a current density of less than 1% of the diffusion limiting current range and at a measuring voltage in the range of 260 to 340 millivolts, measured relative to the reference voltage.

7. The process according to claim 1, including compensating for varying pH values by recalibration of the measuring voltage.

8. The process according to claim 1, including monitoring the temperature of the solution and automatically compensating for temperature changes.

9. The process according to claim 1, wherein the peracetic acid solution is delivered to the cell in a continuous process flow and the potentiostatic amperometry determination is continuously conducted and monitored on the process flow.

10. The process according to claim 1, including a periodic calibration check by providing a solution with a known peracetic acid concentration to the test cell and correcting any measuring sensitivity changes.

11. The process according to claim 10, including monitoring the calibration check results, and when the current density has decreased such that calibration is no longer possible, activating the test electrode by polishing said test electrode.

12. The process according to claim 11, wherein polishing the test electrode includes using an iron oxide-coated abrasive cloth to polish the test electrode.

13. The process according to claim 11, wherein activating the test electrode includes prepolarization of the test electrode prior to polishing said test electrode.

14. The process according to claim 13, wherein the prepolarization of the test electrode is carried out in solutions containing in a solution with a peracetic acid concentration in a range 10 to 30 times greater than the peracetic acid concentration in the solution delivered to the test cell.

15. A test cell apparatus for quantitative determination of peracetic acid in a process solution by potentiostatic amperometry, said test cell apparatus comprising:

a test chamber for receiving a continuous flow of process solution, said test chamber having an inlet and an outlet at opposing ends of said test chamber;

a test electrode and a counterelectrode positioned in said test chamber in spaced-apart relationship;

a reference chamber in fluid communication with said test chamber, said reference chamber including a diaphragm positioned in an aperture connecting said reference chamber to said test chamber;

a reference electrode positioned in said reference chamber;

a control system electrically connected to said test electrode, said counterelectrode, and said reference electrode for receiving and transmitting voltage signals, said control system controlling a test electrode voltage, independently of a reaction mechanism, at a diffusion limiting current range between a no-load voltage and flex points of a current density voltage curve, and calculating the concentration of the peracetic acid in the solution.

16. The test cell apparatus according to claim 15, including a calibration system having a control valve to selectively stop flow of process solution to the test cell and temporarily supply a calibrating solution of known peracetic concentration to the test chamber to calibrate said control system.

17. The test cell apparatus according to claim 15, including a flowmeter mounted on said test chamber and electrically connected to said control system for measuring flow of the process solution and transmitting signals to said control system.

18. The test cell apparatus according to claim 15, including a temperature sensor mounted on said test chamber and electrically connected to said control system for measuring temperature of the process solution and transmitting signals to said control system.

19. The test cell apparatus according to claim 15, wherein said test electrode includes a solid gold jacket engaged over a high-grade steel core.

20. The test cell apparatus according to claim 15, wherein said reference electrode includes a silver/silver chloride electrode.

* * * * *